United States Patent [19]

Raisanen

[11] Patent Number: 5,712,421
[45] Date of Patent: Jan. 27, 1998

[54] MOISTURE ANALYZER

[75] Inventor: Walfred R. Raisanen, Paradise Valley, Ariz.

[73] Assignee: Arizona Instrument Corporation, Phoenix, Ariz.

[21] Appl. No.: 593,834

[22] Filed: Jan. 30, 1996

[51] Int. Cl.⁶ ........................................... G01N 7/00
[52] U.S. Cl. ............................... 73/19.01; 73/76
[58] Field of Search ..................... 73/19.01, 19.12, 73/863.12, 23.2, 73, 76

[56] References Cited

U.S. PATENT DOCUMENTS

| | | | |
|---|---|---|---|
| 2,987,912 | 6/1961 | Jacobson | 73/19 |
| 3,144,765 | 8/1964 | Wollner | 73/76 |
| 3,150,516 | 9/1964 | Linnenbom et al. | 73/19 |
| 3,759,086 | 9/1973 | McAuliffe | 73/19.1 |
| 4,165,633 | 8/1979 | Raisanen | 73/76 |
| 4,457,632 | 7/1984 | Collins et al. | 73/76 X |
| 4,787,052 | 11/1988 | Yamaguchi | 364/550 |
| 4,838,705 | 6/1989 | Byers, Jr. et al. | 73/76 X |
| 4,889,201 | 12/1989 | Oldendorf et al. | 73/73 |
| 5,005,410 | 4/1991 | Webster et al. | 73/335 |
| 5,062,292 | 11/1991 | Kanba et al. | 73/19.1 |
| 5,085,527 | 2/1992 | Gilbert | 73/76 |
| 5,138,870 | 8/1992 | Lyssy | 73/38 |
| 5,154,088 | 10/1992 | Lehnert et al. | 73/866 |
| 5,187,972 | 2/1993 | DeFriez | 73/23.2 |
| 5,191,786 | 3/1993 | Baughman et al. | 73/64.45 |
| 5,218,856 | 6/1993 | Doyle | 73/19.1 |
| 5,253,512 | 10/1993 | LeGigan | 73/73 |
| 5,274,931 | 1/1994 | Ogiri et al. | 34/46 |
| 5,301,440 | 4/1994 | Shimizu et al. | 34/89 |
| 5,340,541 | 8/1994 | Jackson et al. | 422/75 |
| 5,343,735 | 9/1994 | Succi et al. | 73/29.01 |
| 5,400,642 | 3/1995 | Palacios et al. | 73/23.2 |
| 5,402,672 | 4/1995 | Bradford | 73/76 |
| 5,433,105 | 7/1995 | Takahashi et al. | 73/61.46 |
| 5,476,637 | 12/1995 | Fuhrman | 422/68.1 |
| 5,499,532 | 3/1996 | Kaiho et al. | 73/76 |
| 5,511,409 | 4/1996 | Knaebel | 73/28.04 |
| 5,528,923 | 6/1996 | Ledez et al. | 73/19.12 |

OTHER PUBLICATIONS

Quintel Corporation—Karl Fischer Titrators Brochure.

*Primary Examiner*—Hezron E. Williams
*Assistant Examiner*—Jay L. Politzer
*Attorney, Agent, or Firm*—Meschkow & Gresham, P.L.C.

[57] ABSTRACT

Apparatus for determining the actual and proportional amounts of a volatile fluid in a test staple is described. The test staple is stored in a sealed container after being collected and kept in the sealed container through testing. The volatile fluid of interest is evolved from the test sample and a carrier gas transports the volatile fluid past a sensor. The sensor determined the relative amount of the volatile fluid of interest in the carrier gas. The flow rate of the carrier gas is precisely known and is predetermined. A microcomputer is utilized to predict with great accuracy the actual and proportional amount of the volatile fluid in the test sample.

34 Claims, 3 Drawing Sheets ized to the assignee of the present invention, such

MOISTURE ANALYZER

BACKGROUND OF THE INVENTION

This invention pertains to apparatus for determining the actual and proportional amounts of a volatile fluid in a test sample.

DESCRIPTION OF PRIOR ART

Various devices have been developed for determining the quantity of a volatile fluid present in a test sample of material. As pointed out in U.S. Pat. No. 4,838,705 which is assigned to the assignee of the present invention, such determinations are important and/or necessary for various reasons including quality control in manufacturing as well as compliance with various legal or regulatory requirements.

One prior technique for determining the quantity of volatile fluid present is known as the "loss on drying" technique and is described in my U.S. Pat. No. 4,165,633. In that technique, a sample under test is heated to evolve the volatile fluid. The sample is weighed before, during and after testing to determine the change in weight of the sample. Various computational techniques are used to forecast the percentage determination based upon the initial weight loss.

Chemical analysis methods are also used for certain volatile fluids of interest, such as water, through a process known as the "Karl Fischer analysis." These chemical analysis methods rely on the use of reagents which may be toxic. Furthermore, the chemical analysis methods usually require highly skilled operators and time consuming analysis.

In the process which is described in the '705 patent, apparatus is used to collect and weigh the volatile fluid present within a test sample. More specifically, the test sample is heated within a sealed chamber to evolve the volatile fluid. The gaseous form of the fluid is passed through a collector which is sensitive to the volatile fluid of interest. The collector increases weight as the fluid is collected. A weight sensor supporting the collector provides data indicative of the initial weight, interim weight and final weight of the collector during operation of the apparatus. Computational circuitry performs various calculations on the data to provide a predictive and actual determination of the percent by weight of the volatile fluid of interest in the test sample.

Each of the prior methods or techniques may be used to determine the content of various volatile fluids in test samples. One of the most common fluids of interest is water. Accordingly, the illustrative embodiment of my invention is directed to a moisture analyzer, however, the principles of my invention are applicable to other volatile fluids.

Other prior patents which are directed to determining moisture include U.S. Pat. Nos. 5,433,105; 5,343,735; 5,340,541; 5,187,972; 5,274,931; 5,253,512; 5,138,870; 4,787,052 and 4,165,633.

One problem with prior techniques is that the test sample is typically not analyzed immediately after collection but at a later time. More often than not, the test sample is exposed to ambient atmosphere conditions until testing and analysis. This may result in determinations which are inherently inaccurate since in an open environment the volatile fluids of interest may, for example, evolve or be absorbed.

SUMMARY OF THE INVENTION

The present invention is directed to a volatile fluid analyzer in which quantitative test results are provided in a relatively short time and which does not require the use of reagents. More specifically, the present invention utilizes predictive techniques to automatically determine a fluid of interest content in a sample in a short period of time.

In a preferred embodiment of the invention, a moisture analyzer is provided to measure the moisture content of a sample. The sample is placed in an airtight receptacle which in the preferred embodiment is a septum bottle. A counter flow tube arrangement is inserted through the septum. The tube arrangement includes first and second tubes. A carrier gas in injected into the septum bottle through one of the tubes and exhausted through the other tube. The sample is heated by heating the septum bottle. As the sample under test is heated, the volatile fluid, in this case moisture, in the sample under test is evolved into the carrier gas. The gas carries the evolved fluid of interest through a relative humidity sensor. The relative humidity of the carrier gas is measured continuously. The flow rate of the carrier gas is regulated to an accurately known predetermined volumetric rate.

The moisture analyzer predictively determines the total mass by weight of the water in the sample under test by monitoring the relative humidity, the rate of change in the relative humidity and calculating the actual weight in the sample by monitoring the change with time in the relative humidity of the gas stream.

An automatic moisture analyzer in accordance with the invention may be used to determine moisture content in many materials including, but not limited to, plastics, freeze dried drugs, paints and coatings and many other materials that previously were tested using pyrometry and Karl Fischer coulometric analysis.

In accordance with the invention, an inert gas is used to quickly purge the relative humidity sensor of residual moisture. The system is then operated in an automatic calibration mode wherein a known or calibration quantity of moisture is injected into the carrier gas. The moisture content is measured. The measurement is then compared with the known quantity and the result of the comparison is used to factor subsequent test results. In addition, the system stores the result of the calibration test in a memory which then provides a history of the calibration results. After calibration, the system is again purged to remove residual moisture.

In testing samples, a collected sample to be analyzed is placed in an airtight container. The container, which in the illustrative embodiment is a septum bottle, is placed in a heater and the counterflow tube arrangement is inserted into the container. A high flow rate carrier gas purge of the container occurs by flowing the carrier gas into the container through one tube and exhausting it through the other tube. This headspace purge occurs before the sample is heated to a temperature sufficient to evolve the moisture. After purging the container, the flow rate of the carrier gas is reduced to a precisely known flow rate. The relative humidity sensor provides a dynamic and continuous reading of the relative humidity in the carrier gas. The amount of moisture evolved from the sample under test is calculated from the flow rate and the relative humidity readings. The total moisture content may be predicted by characterizing the time dependent changes in the relative humidity.

BRIEF DESCRIPTION OF THE DRAWINGS

The invention will be better understood from a reading of the following detailed description in conjunction with the drawing in which like reference numerals are used to indicate like elements in the various figures and in which.

DETAILED DESCRIPTION

Figure 1:
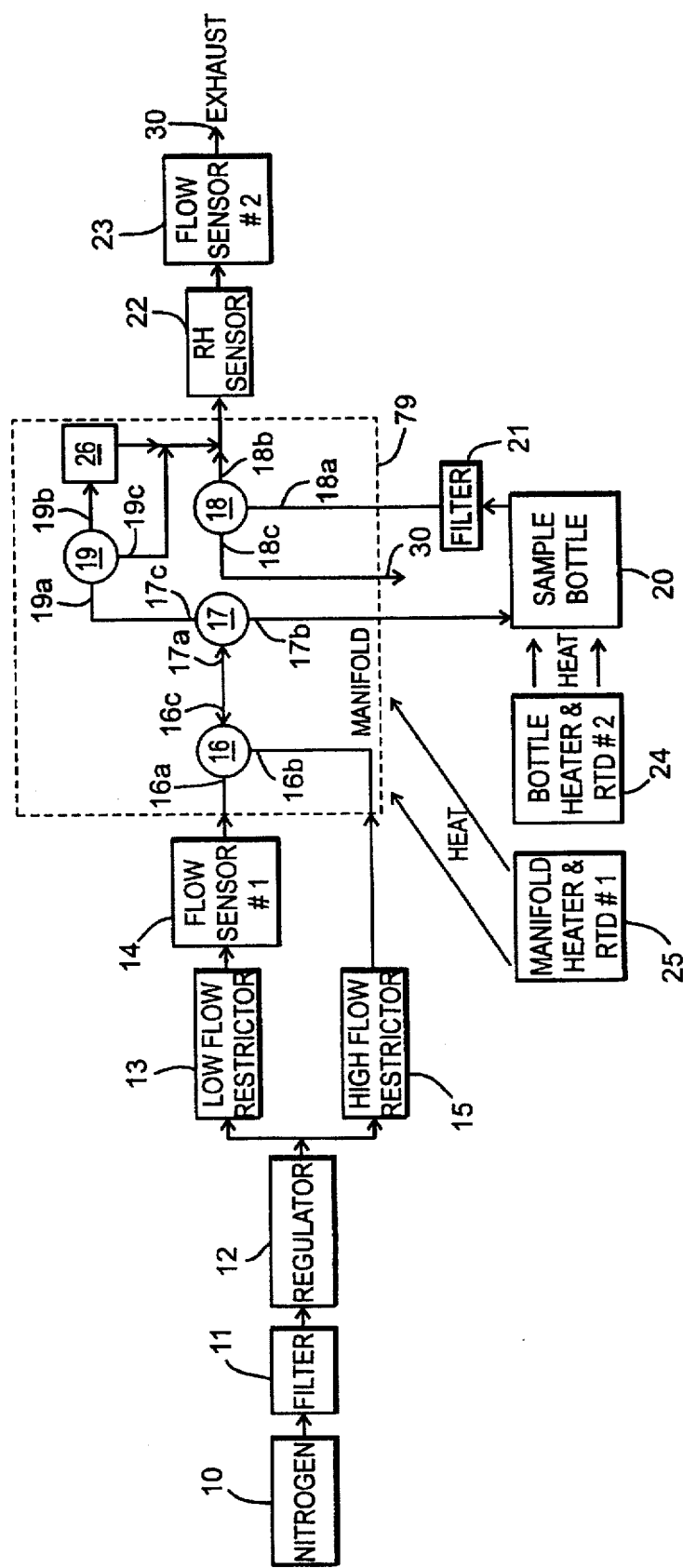
FIG. 1 is a mechanical schematic of a system in accordance with the principles of the invention.

The illustrative moisture analyzer 1 is shown in FIG. 1. A test sample is collected and promptly placed in a septum bottle 20 the test sample remains in the septum bottle 20 after collection and throughout testing. In general, the analyzer evolves the volatile fluid of interest or the water present in a test sample into an inert carrier gas which flows through the septum bottle. The flow rate of the gas is carefully controlled. The carrier gas flows past a relative humidity sensor 22 which provides a continuous indication of the relative amount of the volatile fluid in the gas stream. The humidity sensor 22 is a commercially available capacitance type relative humidity sensor. A conventional microcontroller or computational circuitry 50 of FIG. 3 dynamically converts the relative humidity measurements at the predetermined flow rate into an absolute weight measurement of the water evolved from the sample. By monitoring the rate of change of the relative humidity the microcontroller can predict the total moisture content of the sample. By determining the weight of the test sample prior to subjecting it to evaporative heating, the moisture analyzer can directly provide a measurement of the moisture as a percentage by weight of the sample tested.

In the illustrative embodiment moisture analyzer system 1 a dry nitrogen supply 10 is coupled to the system. Although nitrogen is utilized in the illustrative moisture analyzer 1, it should be understood that any gas which is inert with respect to the volatile fluid of interest in a sample under test may be utilized. The dry nitrogen flows through a 50 micron filter 11 of a type commercially available and then flows to a pressure regulator 12. Pressure regulator 12 is of a type commercially available and maintains the pressure at a predetermined level, typically at 4 psi. Two alternate flow paths are provided from the pressure regulator 12 to establish flows at two different levels. In one path, a flow regulator or restrictor 13 maintains a flow rate at a first predetermined level. For an input pressure of 4 psi, the flow regulator or restrictor 13 provides a flow rate of 190 cc/min. In the second path, a flow regulator or restrictor 15 provides for a significantly higher predetermined flow rate. Typically, the flow rate through the flow regulator or restrictor 15 is approximately 1 liter/min. Each of the flow regulators or restrictors 13 and 15 are commercially available flow regulators of a type which provide a fixed accurate flow rate. Both flow regulators 13 and 15 are coupled to a solenoid valve 16. A flow sensor 14 is disposed between the flow regulator 13 and the solenoid valve 16.

The solenoid valve 16 is utilized to select between two flow rates of the nitrogen through the system. Valve 16 provides either an operational flow through the system from flow regulator 13 or a higher purge flow from flow regulator 15.

Solenoid valve 16 has a first inlet port 16a coupled to the low flow regulator 13 via the flow sensor 14. Valve 16 has a second inlet port 16b coupled to the high flow regulator 15. Solenoid valve 16 includes a single outlet port 16c. The solenoid valve 16 is normally off and the flow through the valve 16 is such that port 16a is coupled to port 16c and port 16b is normally closed. When solenoid valve 16 is energized, port 16b is coupled to port 16c and port 16a is closed. Outlet port 16c of solenoid valve 16 is connected to a sample bottle bypass solenoid valve 17.

Valve 17 has a single inlet 17a and selects between two outlets 17b and 17c. Solenoid valve 17 has inlet port 17a coupled to outlet port 17c when solenoid valve 17 is in in a first energization state such that solenoid valve is not energized. Inlet port 17a is coupled to outlet port 17b when solenoid valve 17 is in a second energization state such that solenoid valve 17 is energized. Outlet port 17b of valve 17 is coupled to sample bottle 20 via a counterflow tube arrangement more specific details of which are set forth hereinafter. The counterflow tube arrangement provides an exhaust flow path from sample bottle 20 which is coupled via a filter 21 to inlet port 18a of a sensor bypass solenoid valve 18. The solenoid valve 18 has two selectable outlets, 18b and 18c. When solenoid valve 18 is in a first energization state such that it is not energized, the inlet 18a is coupled to the outlet port 18c which is coupled to an exhaust 30. When the solenoid valve 18 is in its second energization state such that it is energized, inlet port 18a is coupled to outlet port 18b. Outlet port 18b of the solenoid valve 18 and outlet port 17c of solenoid valve 17 are both coupled to the inlet of a relative humidity sensor 22. The output of relative humidity sensor 22 is coupled to exhaust 30 through a flow sensor 23.

Solenoid valve 19 is provided to selectively operate the analyzer in an automatic calibration function or mode. Valve 19 is normally not energized and in this state, inlet port 19a is connected to outlet port 19c and outlet port 19b is closed. When solenoid valve 19 is energized, inlet port 19a is connected to outlet port 19b and outlet port 19c is closed. With solenoid valve 19 energized, a flow path is established from inlet port 19a through a water injector 26 which has its outlet coupled to relative humidity sensor 22.

Valves 16, 17, 18 and 19 have their various inlets and outlets directly connected in accordance with the connections shown in the drawing by means of a manifold assembly 79. By utilizing a manifold assembly 79, a heater 25 may be formed about the manifold 79 as shown schematically in FIG. 1 so that the nitrogen gas stream is heated.

The sample bottle 20 is placed into a heater assembly 24 so that the sample may be heated to evolve the volatile fluid of interest, e.g., moisture. The temperature of the heater 24 is controlled to a desired temperature set typically from 25° C. to 225° C. The test is automatically terminated when real time analysis of the relative humidity of the gas determines the test endpoint is reached.

The moisture analyzer may be operated in five operational modes: "system dry down", "maintenance dry", "system calibration", "sample bottle purge", and "sample test." The operation of the system in each of these modes will now be described.

In the "system dry down" mode, a high flow rate of dry nitrogen flows through the system to remove any residual volatile fluids, e.g., moisture in the system and in particular to dry the relative humidity sensor 22. In this mode, solenoid valve 16 is energized causing inlet port 16b to be connected to outlet port 16c; solenoid valve 17, 18 and 19 are not energized so that inlet port 17a is coupled to outlet port 17c and inlet port 19a is coupled to outlet port 19c, thereby bypassing the sample bottle 20. With this valve configuration, dry nitrogen flows from source 10 through filter 11, through pressure regulator 12, through the high flow restrictor regulator 15, through valve 16, through valve 17, through valve 19, to the relative humidity sensor 22, through flow sensor 23 to exhaust 30. Valve 18, which has inlet port 18a coupled to outlet 18c and port 18b closed, is bypassed. With this flow path, the dry nitrogen gas from nitrogen source 10 flows at a flow rate of one liter/sec. to dry the system to ensure that it is moisture free prior to analyzing test samples. In this flow configuration, valves 17, 18, and 19 are configured such that there is no flow through sample bottle 20.

Next, the system is configured to a "maintenance dry" mode to keep the components free of moisture. In this mode, valves 17, 18 and 19 remain deenergized as they were in the "dry down" mode. However, valve 16 is now deenergized so that a connection is established between inlet port 16a and outlet port 16c. Inlet port 16b is closed in this mode, thereby cutting off flow from the high flow regulator 15. With this configuration, dry nitrogen flows from source 10, through filter 11, through regulator 12, through low flow restrictor or regulator 13, through flow sensor 14, through valve 16, through valve 17, through valve 19 to outlet 19c, and through the relative humidity sensor 22 and flow sensor 23 to exhaust 30. In this mode, the flow rate through the system is 190 cc/min. This mode is utilized to maintain the relative humidity sensor 22 in a dry state after being initially dried.

The system periodically is operated in an "automatic calibration" mode. In this mode, precise quantities of moisture are injected into the system by moisture injector 26 to measure the response to the sensor 22. In the "automatic calibration" mode, the valves 16, 17 and 18 are in the same energization states that they were in for the "maintenance dry" mode described above. Automatic calibration solenoid valve 19 is energized. With solenoid valve 19 energized, inlet 19a is coupled to outlet 19b and outlet 19c is closed. A flow path is established to the water injector 26 which injects a precise amount of water into the nitrogen gas flow. Then sensor 22 is used to measure the amount of water injected into the system. The amount of water injected is known with great precision. Any discrepancy between the amount of moisture determined and the known amount injected by injector 26 is used to adjust the calibration of the analysis of the readings from sensor 22. A history of the calibration results is stored in a memory.

After the system has been calibrated, it again is dried by operating in a "dry down" mode as described above.

After the system has been dried, calibrated, and dried again, a sample bottle 20 containing a sample under test may be inserted into the bottle heater 24. The bottle 20 takes a few seconds to rise to the temperature of the heater 24 due to thermal delay. During this thermal delay time, a high flow of nitrogen is passed through the bottle 20 to purge the headspace in the bottle 20. To establish a purge flow path through the bottle 20, valves 16 and 17 are energized and valves 18 and 19 are left deenergized. In this configuration, nitrogen flows from source 10 through filter 11, regulator 12, high flow regulator 15, valve 16, valve 17, sample bottle 20, filter 21, valve 18 and out outlet port 18c to exhaust 30. After approximately nine seconds at the high flow rate, the sample bottle 20 has been purged and the thermal delay of the bottle 20 has not yet heated the sample sufficiently to evolve the moisture contained in the sample under test.

The system then enters into the "sample test" mode. In this mode, valve 16 is deenergized and valves 17 and 18 are energized. Dry nitrogen gas flows from source 10 through filter 11, regulator 12, low flow regulator 13, flow sensor 14, valve 16 to outlet 16c, valve 17 to outlet 17b, sample bottle 20, filter 21, valve 18, relative humidity sensor 22 and flow sensor 23 to exhaust 30. This operational mode will be maintained until such time as the analyzer circuitry indicates that the end point of the moisture measurement can be predicted. During this mode, the sample is heated up by means of the heater 24, the volatile fluids of interest in the sample are evolved and carried by the nitrogen flow past the sensor 22.

Flow sensors 14 and 23 are provided in the carrier gas flow path to detect leakage. The flow measured at flow sensors 14 and 23 should at all times be equal. In the event that there is any inequality in the measured flows, a leak has been detected.

A replaceable filter 21 is provided between the sample bottle 20 and the relative humidity sensor 23. The filter 21 is a commercially available product which is used to filter volatile fluids from the exhaust gas other than the volatile fluid of interest. The filter 21 is intended to reduce interference in the measurements resulting from volatiles other than the volatile fluid of interest. In prior moisture analyzers which rely upon collection of the evolved moisture, it is particularly difficult to obtain accurate results for some materials. Nylons in particular contain significant quantities of volatiles other than water which will condense on a collector and yield a false high reading. In the present arrangement, more consistently accurate results are obtained by basing the measurements on relative content of the volatile fluid of interest in the carrier gas on a continuous basis rather than collection of volatiles. The use of the filter 21 causes volatiles other than the volatile fluid of interest, e.g., water, to be collected and filtered out thereby removing this possibility of interference in the measurements.

Figure 2:
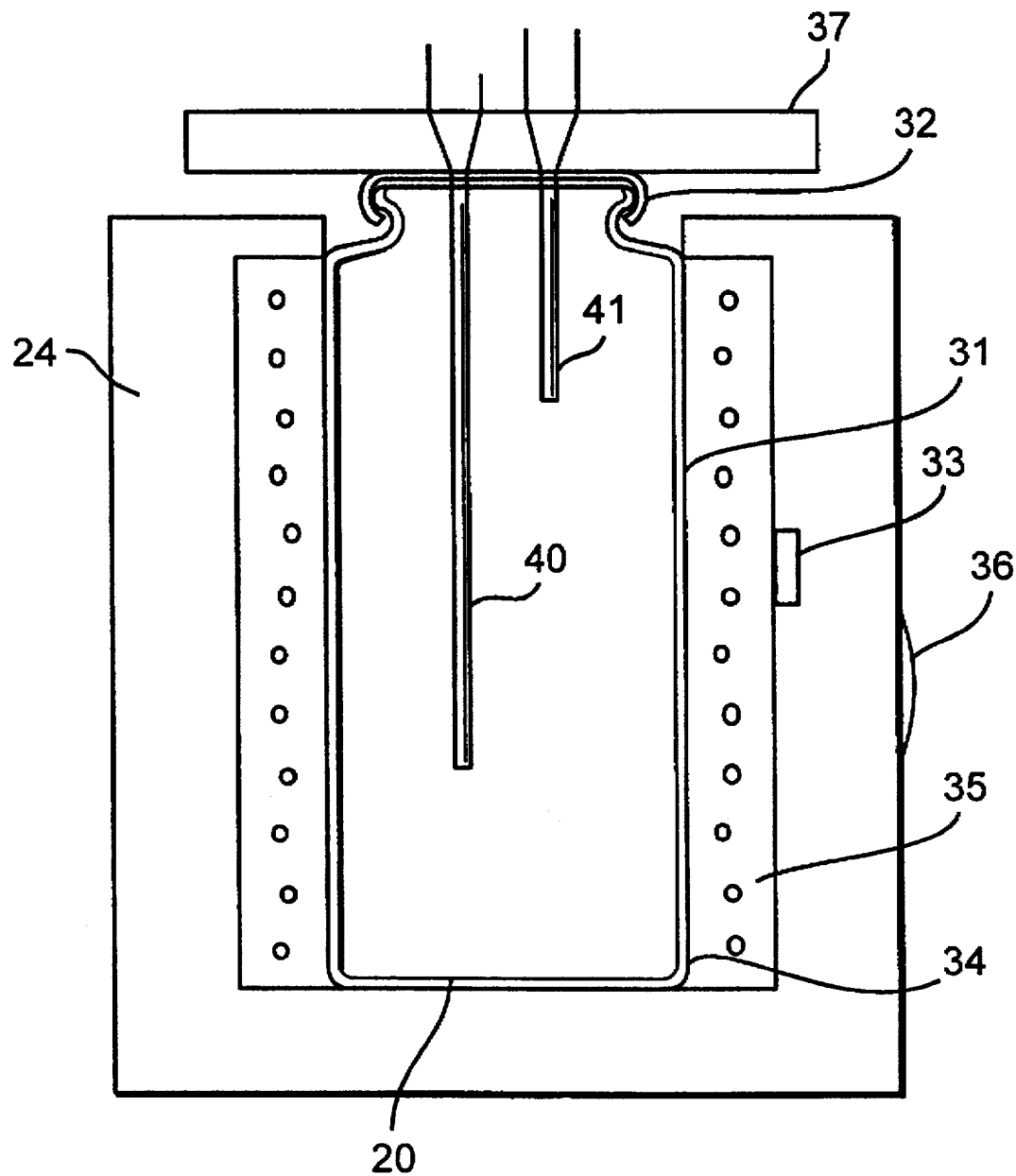
FIG. 2 illustrates in partial cross-section a probe, sample container and heater portion of the system of FIG. 1.

Turning now to FIG. 2, the septum bottle 20 or container used in the moisture analyzer is shown to be a glass septum sealed vial which is commercially available from several sources. The septum bottle 20 includes a vial 31 and a septum seal structure 32.

The bottle heater 24 is provided to heat bottle 20 to evolve the fluid of interest. The heater 24 is designed to provide for rapid, controlled heating. The heater 24 has an opening 34 into which the bottle 20 is placed. The dimensions of the opening 34 are chosen to snugly engage the vial 32 to enhance heat transfer. The heater 24 substantially, completely surrounds the vial 20 except for the top portion of the vial 20. The heater 24 includes a resistance heater element 38 which is immersed in oil 35. An insulated container 36 is provided to retain the heat in the heater 24. A temperature sensor 33 provides signals which are used to control application of power to the heater 24.

A cover 37 for the heater 24 carries a counterflow tube arrangement which in the embodiment shown includes two tubes or hypodermic needles 40 and 41. Each of the tubes or hypodermic needles 40 and 41 are standard commercially available hypodermic needles. Alternatively, a counterflow tube arrangement which utilizes two coaxially aligned tubes is commercially available and may be used.

In using the moisture analyzer 1, the sample to be analyzed is placed into vial 31 and the septum lid 32 is placed on the vial 31. The bottle assembly 20 is placed in the heater 24. The cover 37 is moved onto the septum seal 32. The two tubes or hypodermic needles 40 and 41 penetrate the septum seal 32.

Figure 3:
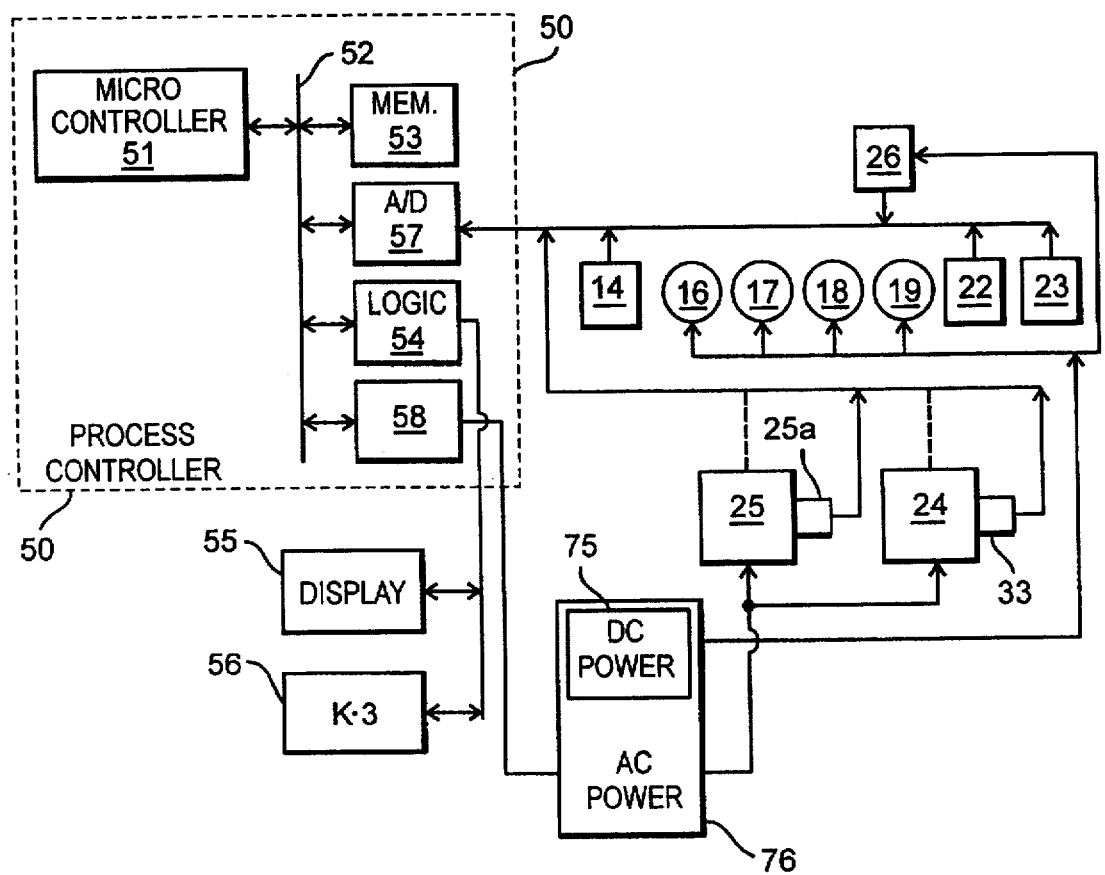
FIG. 3 illustrates in schematic form the electronic control arrangement utilized in conjunction with the system of FIG. 1.

Turning now to FIG. 3, the control system for the illustrative moisture analyzer is shown in block schematic form. A process controller 50 is used to control operation of the moisture analyzer. Controller 50 includes a microcontroller 51. Memory 53 is coupled to the microcontroller 51 via a bus 52. The memory 53 includes EPROM, EEPROM and SRAM types of memory. The operational program for the moisture analyzer is stored in EPROM, operational variables during testing are stored in the SRAM and sensor characterizing constants for each of the various sensors in the moisture analyzer system are stored in the EEPROM. The calibration history of the relative humidity sensor 22 may be stored in the SRAM portion of memory 53.

Peripheral control logic 54 interfaces the microcontroller 51 to a display 55 and a keyboard 56. The display 55 and the keyboard 56 provide the human interface to the system for initiating testing and for entry of test specific data such as the weight of the vial or sample bottle 20 and for display of test results as well as various test messages and related information. Analog to digital interface (A/D) circuits 57 connected to the bus 52 are coupled to the flow sensors 14 and 23 and to the relative humidity sensor 22. Through A/D circuits 57 the microcontroller 51 monitors electrical signals produced by sensors 14 and 23. Microcontroller 51 interprets these signals into instantaneous readings of the gas flow at sensors 14 and 23 and the relative humidity in the gas flow at relative humidity sensor 22. In addition, the A/D circuits 57 are coupled to temperature sensor 33 which is used to monitor the temperature of heater 24 and a temperature sensor 25a which is used to monitor the temperature of the manifold heater 25. The A/D circuits 57 are also coupled to the automatic calibration water injector 26 to monitor the water source for the water injector 26.

The controller 50 also includes peripheral control circuits 58 which are connected to the microcontroller 51 via bus 52. The peripheral control circuits 58 are used to control the application of DC power from power supply 75 to each of the solenoid valves 16, 17 and 18 as well as the automatic calibration circuits. The peripheral control circuits 58 also control application of AC power from AC power source 76 to the bottle heater 24 and the manifold heater 25.

While the system is operating with a test sample, the controller 50 continuously monitors the output of relative humidity sensor 22. Because the flow rate of the nitrogen gas through the sample bottle 20 is accurately known by the use of flow sensor 14, the measured relative humidity as measured by the sensor 22 may be converted into a time dependent rate of transport of the water from the sample under test. The rate of the moisture release from the sample under test may be characterized by an equation which represents an exponential decrease curve. In addition, the curve will converge asymptotically toward a level which represents the total of the moisture in the sample. Thus as the relative humidity decreases toward zero, the moisture content in the sample under test will also approach zero. By calculating slopes of curves which are derived from the measured data controller 50 predicts an end point for the curve which represents the total amount of the moisture contained in the sample under test. Thus, a predictive algorithm may be derived from which the total moisture content of the sample under test may be calculated. By weighing the sample prior to testing and entering the sample weight into the controller 50, controller 50 can directly determine the percentage moisture content for the sample under test. Alternatively, the system can provide a predictive total weight of moisture contained in the sample under test.

The various modes of operation of the system have been described. In operation of the system, the controller 50 is programmed by means of programs stored in the memory to automatically execute certain of those modes. For example, the controller 50 may on a daily basis initially operate in a "system dry down" mode. Then prior to any test measurements being taken, the controller 50 may execute an automatic calibration program to operate the system in the "system calibration" mode. Upon completion of the calibration, the controller 50 then again enters the "system dry down" mode, followed by the "maintenance dry" mode. When a sample bottle 20 is placed in the analyzer, the controller 50 would initially execute the "sample bottle purge" mode and then immediately enter into the "sample test" mode. Upon completion of testing, the controller 50 would again enter the "sample dry down" mode, followed by the "maintenance dry" mode in which it would stay until the next test is to be run.

It will be understood by those skilled in the art to which this invention pertains that various modifications may be made to the illustrative embodiment shown and described without departing from the spirit and scope of the invention. It is intended that the invention be limited only by the claims appended hereto.

What is claimed is:

1. An analyzer for determining the amount of a volatile fluid in a test sample, said apparatus comprising:

a container containing said sample;

means for heating said sample for causing said volatile fluid to evolve from said sample;

means for conveying a carrier gas through said container at a predetermined flow rate to carry said evolved volatile fluid therefrom;

a sensor for continuously sensing the instantaneous relative amount of said volatile fluid in said carrier gas; and computing means coupled to said sensor for determining said volatile fluid content in said test sample.

2. An analyzer in accordance with claim 1, wherein:

said volatile fluid is water.

3. An analyzer in accordance with claim 1, wherein said container comprises:

a septum bottle, said septum bottle receiving said sample.

4. An analyzer in accordance with claim 1 wherein:

said computing means comprises means for predicting the absolute amount of said volatile fluid contained in said sample.

5. An analyzer in accordance with claim 1, wherein:

said computing means determines the time dependent rate of transport of said volatile fluid from said sample, to determine said volatile fluid content.

6. An analyzer in accordance with claim 5, wherein:

said volatile fluid is water.

7. An analyzer in accordance with claim 5, wherein:

said computing means utilizes changes in said time dependent rate to calculate a predicted percentage volatile fluid content of said test sample.

8. An analyzer in accordance with claim 7, wherein:

said volatile fluid is water.

9. An analyzer in accordance with claim 5, wherein:

said computing means utilizes the weight of said test sample and changes in said time dependent rate to calculate a predicted total weight of said volatile fluid in said test sample.

10. An analyzer in accordance with claim 9, wherein:

said volatile fluid is water.

11. An analyzer in accordance with claim 1, wherein:

said gas conveying means comprises a first counterflow tubular assembly having a first tube and a second tube, said assembly being insertable into said container, said first tube conducting said gas into said container and said second tube venting said gas and said volatilized fluid from said container.

12. An analyzer in accordance with claim 11, wherein:

said gas conveying means comprises means for determining the rate of said gas flow to said container.

13. An analyzer in accordance with claim 11, wherein:

said gas conveying means comprises a first flow sensor disposed upstream of said first tube, and a second flow sensor disposed downstream said second tube, said first and second flow sensors each providing signals indicative of gas flow rates; and said computing means being coupled to said first and second flow sensors to provide a signal indication when said first and said second flows have a predetermined relationship.

14. An analyzer in accordance with claim 11 comprising:
a filter disposed between said container and said sensor to filter particulate matter and volatilized fluids other than said volatilized fluid from said gas vented from said septum bottle.

15. An analyzer in accordance with claim 14, wherein:
said gas is nitrogen.

16. A method for determining the volatile fluid content in a material comprising the steps of:
placing a test sample of said material in a container;
evolving said volatile fluid by heating said sample;
conveying a carrier gas through said container at a predetermined flow rate to carry said evolved volatile fluid therefrom;
continuously sensing the instantaneous relative amount of said volatile fluid in said carrier gas; and
utilizing said continuously sensed relative amount to calculate said volatile fluid content in said test sample.

17. A method in accordance with claim 16 comprising:
collecting a test sample of said material, said test sample being placed in said container immediately after collection; and
sealing said container after said placing step and maintaining said container in a sealed state.

18. A method in accordance with claim 16, wherein:
said volatile fluid is water.

19. A method in accordance with claim 16 comprising the step of:
determining the time dependent rate of transport of said volatile fluid from said test sample.

20. A method in accordance with claim 19, wherein:
said volatile fluid content is calculated as a predicted percentage of volatile fluid content.

21. A method in accordance with claim 19 comprising:
weighing said test sample to determine said test sample weight; and
calculating a volatile fluid content in said test sample from said weight and from said time dependent rate.

22. A moisture analyzer comprising:
a sealed container containing a sample under test;
a heater for heating said container;
means for conveying a carrier gas through said container at a predetermined flow rate, said carrier gas carrying moisture from said container;
a relative humidity sensor providing signals representative of the instantaneous relative humidity of said carrier gas; and
microcomputer means coupled to said relative humidity sensor for automatically calculating an end point for transport of moisture from said sample.

23. A moisture analyzer in accordance with claim 22 wherein:
said microcomputer means automatically calculates the amount of water contained in said sample.

24. A moisture analyzer in accordance with claim 22 wherein:
said gas is nitrogen.

25. A moisture analyzer in accordance with claim 24 comprising:
means for bypassing said container;
means for injecting a predetermined quantity of water into said carrier gas; and
said microcomputer means operating to measure the amount of water in said carrier gas and for determining calibration accuracy of said system.

26. A moisture analyzer in accordance with claim 25, wherein:
said microcomputer means includes memory means for storing a calibration history.

27. A moisture analyzer in accordance with claim 26, wherein:
said microcomputer means calculates the amount of moisture in said sample.

28. A method for determining the percent of weight of a fluid of interest in a test sample of known weight, the method comprising the steps of:
(a) maintaining the test sample in a sealed container;
(b) heating the test sample in said container to convert the volatile fluid of interest to a gaseous state;
(c) flowing a conveying gas through said container to exhaust said volatile fluid in said gaseous state from said container;
(d) continuously sensing the instantaneous relative amount of said gaseous state volatile fluid in said conveying gas exhausted from said container; and
(e) utilizing said continuous sensed relative amount to determine the percent by weight of the fluid of interest in the test sample.

29. A method in accordance with claim 28 including the step of:
purging said container with said conveying gas for a predetermined time after initiation of said heating step.

30. A method in accordance with claim 28 wherein:
said fluid of interest is water.

31. A method in accordance with claim 28 comprising the additional step of:
filtering said carrier gas prior to said sensing to remove interfering volatilized fluids.

32. A method in accordance with claim 28 comprising the initial step of:
collecting said sample and storing said sample in said sealed container from the time of collection until completion of testing.

33. A method in accordance with claim 32 wherein:
said container is a septum bottle.

34. An analyzer for determining the amount of a volatile fluid in a test sample, said apparatus comprising:
a container containing said sample;
means for heating said volatile fluid to evolve said volatile fluid from said sample;
a first counter flow tubular assembly having a first tube and a second tube, said assembly being insertable into said container, said first tube conducting a carrier gas into said container at a predetermined flow rate and said second tube venting said gas and said volatile fluid from said container;
a first flow sensor disposed upstream of said first tube, and a second flow sensor disposed downstream said second tube, said first and second flow sensors each providing signals indicated by gas flow rates;
a sensor for continuously sensing the instantaneous relevant amount of said volatile fluid in said carrier gas; and
computing means coupled to said sensor for determining said volatile fluid contents in said test sample and said computing means being coupled to said first and second flow sensors to provide a signal indicating when said first and second flows have a predetermined relationship.

* * * * *

UNITED STATES PATENT AND TRADEMARK OFFICE
CERTIFICATE OF CORRECTION

PATENT NO. : 5,712,421
DATED : 27 January 1998
INVENTOR(S) : Walfred R. Raisanen It is certified that error appears in the above-identified patent and that said Letters Patent is hereby corrected as shown below:

ON THE TITLE PAGE ITEM [57], In the Abstract, line 2, and line 3,

Please delete "staple" and insert --sample-- in both instances.

Signed and Sealed this

Thirty-first Day of March, 1998

Attest:

BRUCE LEHMAN

Attesting Officer

Commissioner of Patents and Trademarks